United States Patent [19]

Barthelemy et al.

[11] Patent Number: 4,883,883

[45] Date of Patent: Nov. 28, 1989

[54] N[METH)ALLYLOXY(METH)ALLYL-PHENYL]MALEIMIDES AND THERMOSETTING IMIDO COPOLYMERS PREPARED THEREFROM

[75] Inventors: Pascal Barthelemy, Lyons; Michel Crochemore, Chaponost, both of France

[73] Assignee: Rhone-Poulenc Chimie, Courbevoie, France

[21] Appl. No.: 134,088

[22] Filed: Dec. 17, 1987

[30] Foreign Application Priority Data

Dec. 17, 1986 [FR] France ............................ 86 17916

[51] Int. Cl.$^4$ .................. C07D 207/28; C07G 101/44
[52] U.S. Cl. .................................. 548/549; 548/548; 562/433; 528/26; 528/322
[58] Field of Search ................. 548/549, 548; 562/432

[56] References Cited

U.S. PATENT DOCUMENTS

| | | | |
|---|---|---|---|
| 3,053,851 | 9/1962 | Ladd ..................... | 548/549 |
| 3,265,708 | 8/1966 | Stiteler ................... | 548/549 |
| 3,763,081 | 10/1973 | Holub et al. . | |
| 4,316,002 | 2/1982 | Cassat et al. . | |
| 4,361,690 | 11/1982 | Locatelli . | |
| 4,400,521 | 8/1983 | Oba et al. ............. | 548/549 |
| 4,500,719 | 2/1985 | Oba et al. ............. | 548/522 |
| 4,742,141 | 5/1988 | Dien et al. ............ | 526/262 |

FOREIGN PATENT DOCUMENTS 0077840 5/1983 European Pat. Off. .
0141765 6/1985 European Pat. Off. .
2046263 11/1980 United Kingdom .

OTHER PUBLICATIONS

Chem Abstracts vol. 71, 1969, p. 290, 3164h N-(-Vinyloxyphenyl) phthalimides.
Chem Abstracts vol. 79, 1973, p. 455, 78311c Vinyl Ethers of imidophenols.
Chem Abstracts vol. 92, 1980, p. 581, 6180e Reaction of acrylidenevinyloxyanilines with anhydrides of unsaturated dicarboxylic acids.
Streitwiser et al., *Introduction to Organic Chemistry*, 2nd ed., MacMillian Publishing Co. Inc., New York, 1981, pp. 1012-1013.

*Primary Examiner*—John C. Bleutge
*Assistant Examiner*—R. Dean, Jr.
*Attorney, Agent, or Firm*—Burns, Doane, Swecker & Mathis

[57] ABSTRACT

Novel N-[(meth)allyloxy-mono-/di(meth)allylphenyl]-maleimides, in admixture with at least one N-[(meth)allyloxyphenyl]maleimide, are reacted with at least one bismaleimide, and optionally a hydroxylated organosilicon compound, in the presence of an imidazole compound, to obtain mechanically improved thermosetting imido copolymerizates well adapted for the production of, e.g., coatings, adhesive bondings, laminates and composites.

4 Claims, No Drawings

N[(METH)ALLYLOXY(METH)ALLYLPHENYL]-MALEIMIDES AND THERMOSETTING IMIDO COPOLYMERS PREPARED THEREFROM

CROSS-REFERENCE TO RELATED APPLICATIONS

Copending applications, Ser. No. 06/880,838, filed July 1, 1986, now U.S. Pat. No. 4,788,295, Ser. No. 134,068 pending, and Ser. No. 134,043 now U.S. Pat. No. 4,839,440, filed 12/17/87, the latter two filed concurrently herewith and all assigned to the assignee hereof.

BACKGROUND OF THE INVENTION

1. Field of the Invention:

The present invention relates to novel mixtures of N-substituted monomaleimides and to novel thermosetting compositions based on such mixtures, which novel compositions have improved mechanical properties.

2. Description of the Prior Art:

N-substituted maleimides are a known family of chemical compounds and the N,N'-disubstituted bis-maleimides are especially useful for the preparation of thermosetting polymers, the polybis-maleimides.

The monomaleimides are also known to this art. For example, U.S. Pat. No. 2,444,536 describes a process for the preparation of N-arylmaleimides.

Some monomaleimides are useful in the agrochemical field, as insecticides or fungicides. Others may be used for preparing polymers which can be crosslinked under the influence of light.

The monomaleimides may also be employed in admixture with the bis-maleimides for the production of thermosetting polymers.

SUMMARY OF THE INVENTION

A major object of the present invention is the provision of novel admixture of N-substituted monomaleimides useful for the formulation of improved thermosetting compositions.

Briefly, the present invention features a mixture of (i) an N-(meth)allyloxyphenylmaleimide having the structural formula:

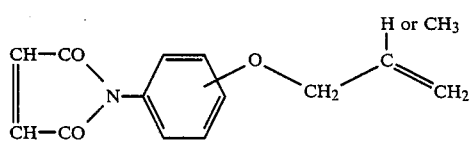

in which the allyloxy or methallyloxy substituent is in the ortho, meta or para position relative to the carbon atom of the benzene ring that is bonded to the nitrogen atom, with:

(ii) at least one mono-(meth)allylated compound having the structural formula:

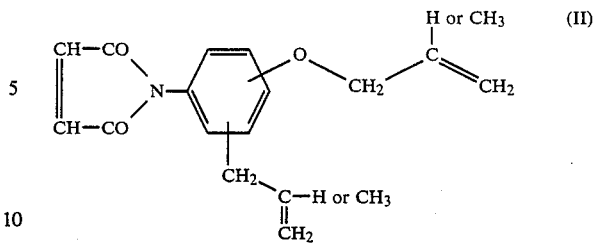

and, optionally, with (iii) one or more di-(meth)allylated compounds having the structural formula:

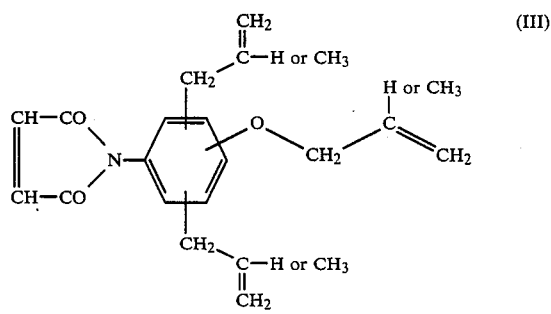

DETAILED DESCRIPTION OF THE PREFERRED EMBODIMENTS OF THE INVENTION

More particularly according to the present invention, the proportions of the various constituents in the mixture of the compounds of formulae (I), (II) and optionally (III) may vary over wide limits. Advantageously, the proportions of the constituents are selected from between the following limits (expressed as percentages by weight of each of the constituents in the mixture):

(a) at least 30%, and preferably from 50% to 80% of the N-(meth)allyloxyphenylmaleimide of formula (I);

(b) from 5 to 50%, and preferably from 10% to 35%, of the mono-(meth)allylated compound(s) of formula (II); and (c) from 0% to 20%, and preferably from 0% to 15%, of the di-(meth)allylated compound(s) of formula (III), with the proviso that the sum of the constituents in each mixture is equal to 100% by weight.

The mixtures according to the invention, based on N-(meth)allyloxyphenylmaleimide and the (meth)allyl-substituted derivative(s) thereof, are conveniently formulated, for example, by intimately admixing the constituents having the formulae (I), (II) and optionally (III), said constituents being prepared separately.

The maleimides of formula (I) are conveniently prepared from aminophenols (ortho, meta or para), according to the Claisen reaction.

For example, an aminophenol (the amine group of which is first blocked by reaction with acetic anhydride such as to form acetamidophenol) can be reacted with an allyl or methallyl halide (most typically the bromide), as the case may be, dissolved in acetone and in the presence of dipotassium carbonate. The amine group is then regenerated by hydrolysis.

The corresponding maleimide is then prepared in conventional manner by reacting, in solution, previously prepared allyloxyaniline or methallyloxyaniline with maleic anhydride in the presence of acetic anhydride, triethylamine and a nickel salt (especially nickel acetate).

N-allyloxyphenylmaleimide or N-methallyloxyphenylmaleimide is thus produced.

N-(4-allyloxyphenyl)maleimide is a mustard yellow-colored solid having a melting point of approximately 103° C.

The NMR analysis is in agreement with the following structure:

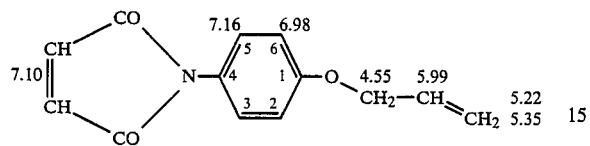

$^1$H NMR; solvent: DMSO d6; reference: hexamethyldisiloxane (HMDS):
7.16 (2H,m): H 3.5;
7.10 (2H,s): maleimido;
6.98 (2H,m): H 2.6;
5.99 (1H,m): —CH═;
5.35 and 5.22 (2H,dd): ═CH$_2$;
4.55 (2H,d): OCH$_2$.

N-(3-allyloxyphenyl)maleimide is a viscous orange-yellow liquid which crystallizes slowly at ambient temperature and which boils at approximately 150° C. at a pressure of 20 Pa.

NMR analysis is in agreement with the following structure:

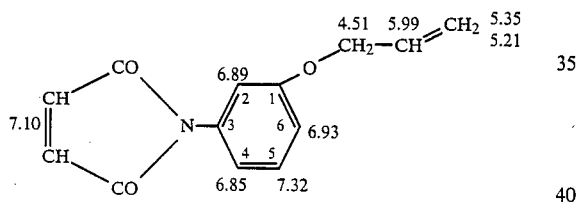

$^1$H NMR; solvent: DMSO d6; reference: HMDS
6.85, 6.89 and 6.93 (3H,m): H4, H2 and H6;
7.10 (2H,s): maleimido;
7.32 (1H,t): H5;
5.99 (1H,m): —CH═;
5.35 and 5.21 (2H,dd): ═CH$_2$;
4.51 (2H,d): OCH$_2$.

N-(2-allyloxyphenyl)maleimide is a pale yellow crystalline solid having a melting point of approximately 82° C. and a boiling point of from 148° C. to 155° C. at a pressure of 20 Pa.

NMR analysis is in agreement with the following structure:

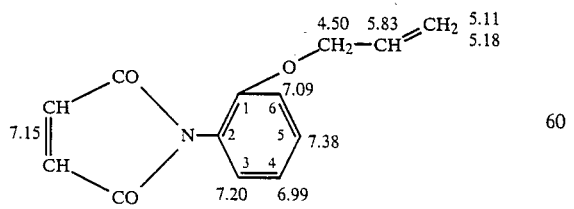

$^1$H NMR; solvent: DMSO d6; reference: HMDS
7.38 (1H,dt): H5;
7.20 (1H,dd): H3;
7.15 (2H,s): maleimido;
7.09 (1H,dd): H6;
6.99 (1H,dt): H4;
5.83 (1H,m): —CH═;
5.18 and 5.11 (2H,dd): ═CH$_2$;
4.50 (2H,d): OCH$_2$.

N-(4-methallyloxyphenyl)maleimide is a beige-colored solid having a melting point of 64° C.

NMR analysis is in agreement with the following structure:

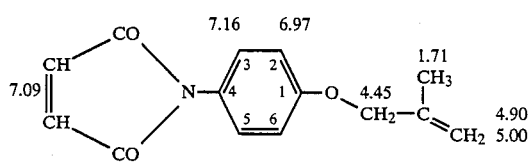

$^1$H NMR; solvent: DMSO d6; reference: HMDS:
7.16 (2H,d): H 3.5;
7.09 (2H,s): maleimido;
6.97 (2H,d): H 2.6;
4.90 and 5.00 (1H,s): CH$_2$═;
4.45 (2H,s): OCH$_2$;
1.71 (3H,s): CH$_3$.

N-(3-methallyloxyphenyl)maleimide is a beige-colored solid having a melting point of 39° C.

NMR analysis is in agreement with the following structure:

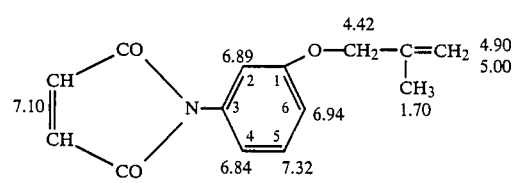

$^1$H NMR; solvent: DMSO d6; reference: HMDS:
7.32 (1H,t): H5;
7.10 (2H,s): maleimido;
6.94 (1H,d): H6;
6.89 (1H,s): H2;
6.84 (1H,d): H4;
4.90 and 5.00 (1H,1): CH$_2$═;
4.42 (2H,s): OCH$_2$;
1.70 (3H,s): CH$_3$.

N-(2-methallyloxyphenyl)maleimide is a beige-colored solid having a melting point of 96° C.

NMR analysis is in agreement with the following structure:

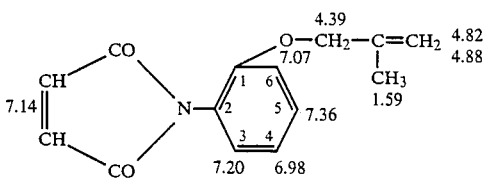

$^1$H NMR; solvent: DMSO d6; reference: HMDS:
7.36 (1H,t): H5;
7.20 (1H,d): H3;
7.14 (2H,s): maleimido;
7.07 (1H,d): H6;
6.98 (1H,t): H4;
4.82 and 4.88 (1H,s): CH$_2$═;
4.39 (2H,s): OCH$_2$;

1.59 (3H,s): CH$_3$.

In a preferred embodiment of the present invention, the mixture of N-(meth)allyloxyphenylmaleimide of formula (I) with one or more (meth)allyl-substituted derivatives of formula(e) (II) and optionally (III) is in the form of a crude product resulting from the process described immediately hereinbelow.

This process is characterized in that it includes the following 3 stages, which are carried out in sequence in the same reactor:

(1) the first stage comprises reacting, in a solvent medium, an aminophenol with maleic anhydride, at a temperature ranging from 20° C. to 200° C., for a period of time ranging, depending on the temperature selected, from 30 minutes to 2 hours (this first stage provides a first reaction medium containing an N-(hydroxyphenyl)maleamic acid);

(2) the second stage comprises (meth)allylating the aforementioned acid by reacting said first reaction medium with a (meth)allyl halide, at a pH which must be adjusted and maintained at a constant value of from 7 to 14 by adding a defined amount of an aqueous alkaline solution, at a temperature ranging from 40° C. to 150° C., and after the acidification and removal of the aqueous phase (this second stage provides a second organic reaction medium containing an N-[(meth)allyloxyphenyl]maleamic acid, one or more N-[(meth)allyloxy(meth)allylphenyl]maleamic acids and optionally one or more N-[(meth)allyloxydi(meth)allylphenyl]maleamic acids);

(3) the third stage comprises cyclizing the aforementioned maleamic acids by reacting said second reaction medium with an anhydride of a lower carboxylic acid, in the presence of a tertiary amine and optionally a catalyst, and then removing the reaction solvent (this third stage provides a crude reaction product which is a mixture formed from at least 30% by weight, and preferably from 50% to 80% by weight, of N-(meth)allyloxyphenylmaleimide, from 5% to 50% by weight, and preferably from 10% to 35% by weight, of one or more N-[(meth)allyloxy(meth)allylphenyl]maleimides and from 0% to 20% by weight, and preferably from 0% to 15% by weight, of one or more N-[(meth)allyloxydi(meth)allylphenyl]maleimides.

The 3 stages described above are carried out in sequence, in a single solvent, in order to achieve greater simplicity in the process; however, it is possible to change the solvent during any particular stage without encountering difficulty. The choice of solvent is very wide; however, as the second stage is performed in an aqueous/organic two-phase medium, it may be desirable to employ a water-immiscible organic solvent which simplifies considerably the treatment of the reaction mass. Exemplary of the water-miscible or -immiscible solvents which can be used, preferred are those which dissolve the starting aminophenol under the temperature conditions selected for the synthesis. Among these solvents, representative are, for example: alcohols (such as, for example, methanol, ethanol and butanol); ketones (such as, for example, acetone, methyl ethyl ketone and methyl isobutyl ketone); nitriles (such as, for example, benzonitrile, propionitrile and acetonitrile); esters (such as, for example, ethyl acetate and butyl acetate); aromatic solvents (such as, for example, anisole and chlorobenzene); and halogenated hydrocarbons (such as, for example, chloroform, dichloromethane and dichloroethane).

With respect to the first stage of the process, the concentration of the starting reagents in the solvent is not critical. However, for productivity reasons, it is neither advisable to dilute the reaction medium too much, nor is it advisable to concentrate it too much, for reasons of ease of stirring. In this first stage, maleic anhydride is employed in quantities at least equal to one mole per mole of aminophenol; larger quantities on the order of 1.01 to 1.5 moles per mole of aminophenol are typically employed. Additionally, the temperature preferably ranges from 40° C. to 60° C.

With respect to the second stage, the amount of aqueous alkaline solution, for example, an aqueous NaOH solution, required, on the one hand, to salify the N-(hydroxyphenyl)maleamic acid and, on the other hand, to provide the desired pH, is first added to the reaction medium. The pH will be maintained constant throughout the reaction period by adding sodium hydroxide; preferentially, the pH is adjusted and maintained at a constant value of from 10 to 12. The allylation reaction is preferably carried out using (meth)allyl bromide or chloride. The quantity of (meth)allyl halide is on the order of 1.5 to 10 moles per mole of phenolic OH group and preferably on the order of 2 to 4. The excess of this reagent may be recovered at the end of the operation and recycled into a following operation. The period over which (meth)allyl halide is added is not critical and advantageously ranges from 1 hour to 5 hours and preferably from 2 hours to 4 hours. In this second stage, the temperature preferably ranges from 60° C. to 100° C. It should be noted that at the end of this stage, the aqueous phase is acidified to a pH of approximately 1 using common acids, preferably inorganic oxyacids or hydracids. The aqueous layer is removed and the organic layer remains in the reactor.

With respect to the third stage of the process, acetic anhydride is advantageously used as the lower carboxylic acid anhydride, in quantities at least equal to one mole per mole of HOOC—CH=CH—CO—NH— group to be cyclized. Larger quantities on the order of 1.05 to 1.5 moles per maleamic group are generally employed.

Exemplary of the tertiary amines suitable therefor, particularly representative are the trialkylamines and N,N-dialkylanilines in which the alkyl radicals contain from 1 to 12 carbon atoms. It is advantageous to employ triethylamine or N,N-dimethylaniline. The quantities of tertiary amine range from 0.05 to 2 moles per mole of HOOC—CH=CH—CO—NH— group.

Exemplary of the catalysts therefor, representative are the nickel salts of carboxylic acids, hydrated if required, and the chelated forms of such metal. The acetate and acetylacetonate are particularly well suited. These catalysts are employed in very small amounts, on the order of 0.05 to 1.5 g per mole of HOOC—CH=CH—CO—NH— group and preferably on the order to 0.1 to 0.8 g.

In this third stage, the temperature is not critical and has no effect on the reaction rate. This temperature may, for example, range from 40° C. to 150° C. and preferably from 60° C. to 80° C. At the end of this stage, the solvent is removed by vacuum distillation and the crude reaction product, having the appearance of an oil, is obtained.

In a very preferred embodiment of the present invention, the process described above is very suitable for the preparation, beginning with meta-aminophenol, of mixtures based on the following compounds:

N-[3-(meth)allyloxyphenyl]maleimide+N-[3-(meth)allyloxy-4-(meth)allylphenyl]maleimide+N-[3-(meth)allyloxy-6-(meth)allylphenyl]maleimide+, where appropriate, N-[3-(meth)allyloxy-4,6-di-(meth)allylphenyl]maleimide.

It will be appreciated that using ortho-aminophenol as the starting material results in mixtures based on the following compounds:

N-[2-(meth)allyloxyphenyl]maleimide+N-[2-(meth)allyloxy-3-(meth)allylphenyl]maleimide+N-[2-(meth)allyloxy-5-(meth)allylphenyl]maleimide+, where appropriate, N-[2-(meth)allyloxy-3,5-di-(meth)allylphenyl]maleimide.

It will also be appreciated that using para-aminophenol as the starting material results in mixtures based on the following compounds:

N-[4-(meth)allyloxyphenyl]maleimide+N-[4-(meth)allyloxy-3-(meth)allylphenyl]maleimide+, where appropriate, N-[4-(meth)allyl-oxy-3,5-di(meth)allylphenyl]maleimide.

Formulating one or more bis-maleimides with the above mixtures of monomaleimides of general formulae (I), (II)+optionally (III) provides novel thermosetting compositions useful for molding or impregnation. These novel thermosetting compositions have improved mechanical properties vis-a-vis the compositions which do not include the novel mixtures of monomaleimides according to the invention.

Thus, this invention also features novel thermosetting compositions comprising the product of reaction, at a temperature ranging from 50° to 300° C., among the following constituents ($\alpha$), ($\beta$), optionally ($\gamma$), and ($\delta$):

($\alpha$) one or more bis-imides having the general formula (IV):

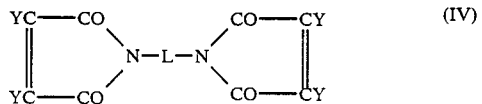

in which Y is a hydrogen atom or a methyl group; and L is a divalent hydrocarbyl radical, such as a cyclohexylene radical; a phenylene radical; a 4-methyl-1,3-phenylene radical; a 2-methyl-1,3-phenylene radical; a 5-methyl-1,3-phenylene radical; a 2,5-diethyl-3-methyl-1,4-phenylene radical; or a radical of the formula (V):

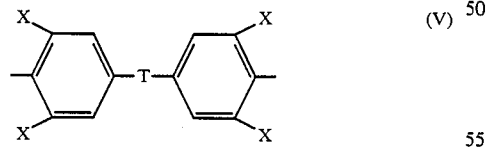

in which T is a simple valence bond or an atom or group below:

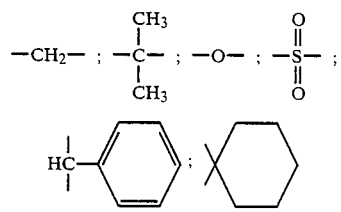

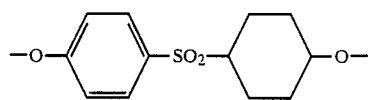

and X is a hydrogen atom or a methyl, ethyl or isopropyl radical;

($\beta$) a mixture of N-(meth)allyloxyphenylmaleimide of formula (I) with one or more (meth)allylated compounds of formulae (II) and optionally (III) as described above;

($\gamma$) optionally, an organosilicon compound containing at least one hydroxyl group bonded to a silicon atom; and ($\delta$) an imidazole compound.

Exemplary of the bis-maleimides of formula (IV), representative are:

N,N'-metaphenylenebis-maleimide,
N,N'-paraphenylenebis-maleimide,
N,N'-4,4'-diphenylmethanebis-maleimide,
N,N'-4,4'-diphenyletherbis-maleimide,
N,N'-4,4'-diphenylsulfonebis-maleimide,
N,N'-1,4-cyclohexylenebis-maleimide,
N,N'-4,4'-(1,1-diphenylcyclohexylidene)bis-maleimide,
N,N'-4,4'-(2,2-diphenylpropane)bis-maleimide,
N,N'-4,4'-triphenylmethanebis-maleimide,
N,N'-1,3-(4-methylphenylene)bis-maleimide, and
N,N'-1,3-(2-methylphenylene)bis-maleimide.

Among these bis-maleimides, N,N'-4,4'-diphenylmethanebis-maleimide, N,N'-1,3-(4-methylphenylene)bis-maleimide, N,N'-1,3-(2-methylphenylene)bis-maleimide, and mixtures thereof, are the more particularly preferred.

These bis-maleimides may be prepared according to the processes described in U.S. Pat. No. 3,018,290 and British Pat. No. 1,137,290.

The hydroxylated organosilicon compounds which are optionally included in the thermosetting compositions of the invention are known compounds having the following general formula (VI):

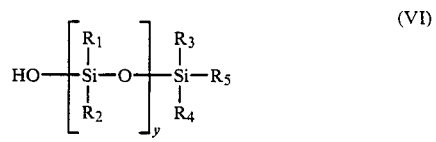

in which $R_1$, $R_2$, $R_3$, $R_4$ and $R_5$, which may be identical or different, are each a hydroxyl group or an —$OR_6$ radical wherein $R_6$ is a straight or branched chain alkyl radical containing from 1 to 6 carbon atoms or a phenyl radical; a hydrogen atom; a straight or branched chain alkyl radical containing from 1 to 6 carbon atoms, or a substituted such alkyl radical bearing one or more chlorine or fluorine atom substituents or a —CN group; a straight or branched chain alkenyl radical containing from 2 to 6 carbon atoms; a phenyl radical, or a substituted phenyl radical bearing one or more alkyl and/or alkoxyl substituents containing from 1 to 4 carbon atoms, or by one or more chlorine atoms; and y is an integer or a real number ranging from 0 to 1,000.

For a given organosilicon compound of formula (VI), y is in fact always an integer; however, in such case these are polymeric compounds (when y is greater than 1), and a single molecule is rarely obtained. Most frequently, a mixture of compounds of the same chemical structure which differ by the number of recurring units in their molecule are obtained; this gives rise to an average value for y, which may be an integer or a real number.

The hydroxylated organosilicon compounds of the above type may be characterized by the ratio of the weight of hydroxyl groups contained therein to the total weight of their molecule.

The presence of a hydroxylated organosilicon compound is a measure which especially makes it possible to facilitate conversion of compounds containing maleimide groups into the molten state and also to impart a greater fluidity in the molten state to the resulting thermosetting resin during the preparation of the thermosetting compositions according to the present invention.

When the organosilicon compounds are indeed used, the compounds which are preferred according to this invention are those described above in which the proportion by weight of hydroxyl groups in the molecule is at least equal to 0.05% and preferably at least 0.1%.

Exemplary of such preferred organosilicon compounds, particularly well suited are compounds of the formula (VI) in which $R_1$, $R_2$, $R_3$ and $R_4$, which may be identical or different, are each a straight or branched chain alkyl radical containing from 1 to 6 carbon atoms or a straight or branched chain alkenyl radical containing from 2 to 6 carbon atoms, or a phenyl radical; $R_5$ is a hydroxyl group; and y is an integer or a real number ranging from 0 to 250.

Therefore, these are silanediols when y is equal to 0, or, alternatively, polysiloxanediols when y is other than 0.

The preparation of such compounds is described in the text by W. Noll, *Chemistry and Technology of Silicones* (English translation of the German publication of 1968), published by Academic Press, New York.

The organosilicon compounds which are very particularly well suited according to this invention are, for example, selected from among:
 diethylsilanediol
 diphenylsilanediol
 methylphenylsilanediol
 1,1,3,3-tetramethyldisiloxane-1,3-diol
 1,1-dimethyl-3,3-diphenyldisiloxane-1,3-diol
 1,3-dimethyl-1,3-diphenyldisiloxane-1,3-diol
 1,1,3,3,5,5-hexamethyltrisiloxane-1,5-diol
 1,1,3,3,5,5,7,7-octamethyltetrasiloxane-1,7-diol
 1,1,2,3,5,5,7,7,9,9-decamethylpentasiloxane-1,9-diol
 1,1,3,3,5,5,7,7,9,9,11,11-dodecamethylhexasiloxane-1,11-diol
 1,3,5,7,9-pentamethyl-1,3,5,7,9-pentaphenylpentasiloxane-1,9-diol
and the corresponding higher homologs thereof.

The hydroxylated organosilicon compounds which are especially preferred may also be mixtures of two or more of the abovementioned compounds. Thus, for convenience, the commercially available hydroxylated polysiloxane oils or resins may be used. These are, in particular, α,ω-dihydroxylated polymethylpolysiloxane oils containing from 0.2 to 0.3% by weight of hydroxyl groups (Rhône-Poulenc oil 48 V 500), or 10 to 12% by weight of hydroxyl groups (Rhône-Poulenc oil 48 V 50), or α,ω-dihydroxylated methylphenylpolysiloxane oils or resins containing 4.5% to 5% by weight of hydroxyl groups (Rhône-Poulenc oil 50606), or from 7.5 to 8.5% by weight of hydroxyl groups (Rhône-Poulenc resin 50305). These commercially available oils or resins are given by way of example; however, there are others which may be equally well suited.

In the compositions according to the present invention formulated from one or more bis-imides of formula (IV) and the mixture ($\beta$), the amounts of the respective components are selected such as to provide the following percentages by weight relative to the total weight of said components:
 from 50 to 95% of bis-imide(s); and
 from 5 to 50% of mixture ($\beta$).

In the compositions of this invention prepared from one or more bis-imides of formula (II), with the mixture ($\beta$) and with a hydroxylated organosilicon compound of formula (IV), the amounts of the respective components are selected such as to provide the following percentages by weight relative to the total weight of said components:
 from 40 to 90% of bis-imide(s);
 from 5 to 40% of mixture ($\beta$); and
 from 5 to 40% of hydroxylated organosilicon compound.

In order to formulate compositions according to the invention which are of the above type, having higher flexural property values in the heated state, it is preferable to employ a proportion of organosilicon compound constituting 5 to 20% by weight relative to the total weight of the bis-imide(s), the mixture ($\beta$), and the hydroxylated organosilicon compound.

The imidazole compound ($\delta$) corresponds to the following general formula (VII):

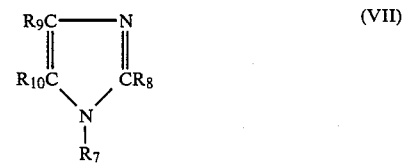

in which $R_7$, $R_8$, $R_9$ and $R_{10}$, which may be identical or different, are each a hydrogen atom, an alkyl or alkoxy radical containing from 1 to 20 carbon atoms, a vinyl radical, a phenyl radical or a nitro group, with the proviso that $R_9$ and $R_{10}$ may together form, with the carbon atoms from which they depend, a single ring member such as, for example, a benzene ring, and with the further proviso that $R_7$ may constitute a carbonyl group linked to a second such imidazole ring.

As specific examples of these imidazole compounds, particularly representative are imidazole or glyoxaline, 1-methylimidazole, 2-methylimidazole, 1,2-dimethylimidazole, 1-vinylimidazole, 1-vinyl-2-methylimidazole, benzimidazole and carbonyldiimidazole.

The imidazole compound is employed in catalytic amounts. Depending on the nature of the imidazole compound and depending on the polymerization rate desired, the imidazole compound is employed in a proportion of from 0.01 to 1% by weight relative to the total weight of the reagents ($\alpha$)+($\beta$)+optionally ($\gamma$).

The imidazole is preferably employed in a proportion of 0.02 to 0.5% by weight relative to the same mixture.

The compositions according to the invention may also contain a N,N′,N″-tris(hydroxyalkyl)hexahydrotriazine. N,N′,N″-tris(hydroxyethyl)hexahydro-1,3,5-triazine, N,N′,N″-tris(hydroxypropyl)hexahydro-1,3,5-triazine and N,N′,N″-tris(hydroxybutyl)hexahydro-1,3,5-triazine are more particularly employed.

N,N',N"-tris(hydroxyethyl)hexahydro-1,3,5-triazine, which is commercially available, will preferably be employed.

When it is present, the N,N',N"-tris(hydroxyalkyl)-hexahydrotriazine imparts better adhesiveness to the subject thermosetting compositions, as well as an improvement in thermomechanical properties, especially flexural strength.

From 0 to 5% by weight of the N,N',N"-tris(hydroxyalkyl)hexahydrotriazine relative to the total weight of the reagents (α)+(β)+optionally (γ) is typically present.

In order to attain a high efficacy, it is preferred to employ from 0.5 to 2% by weight of the N,N',N"-tris(hydroxyalkyl)hexahydrotriazine relative to the same mixture.

After heat treatment, the compositions according to the invention provide higher values for the mechanical properties, especially flexural properties, at ambient temperature and in the heated state (generally 250° C.) than those obtained using the prior art compositions, such as those described in French patent application No. 83/17,218, published under No. 2,553,780.

Various adjuvants may also be incorporated into the compositions according to the invention. These adjuvants which are typically employed and which are well known to this art may be, for example, stabilizers or degradation inhibitors, lubricants or mold release agents, dyes or pigments, powdery or particulate fillers such as silicates, carbonates, kaolin, chalk, powdered quartz, mica or glass microbeads, and the like. Adjuvants which modify the physical structure of the final product may also be incorporated, such as, for example, pore-forming agents or fibrous reinforcing agents such as carbon, polyimide or aromatic polyamide fibrils, whiskers, and the like.

The production process is such that the thermosetting resin, which is ready for use, has sufficient flexibility and binding capacity in thin layer form. Additionally, in order to obtain a homogeneous material after lamination, any reactions producing very volatile compounds at the heat treatment temperatures must not be significant. To this end, when the starting reagents comprise a silanediol, it is desirable to first carry out the major part of the oligomerization reaction which releases water as byproduct; this water may be removed more easily during the production of the resin.

According to a first method, a mixture of compounds containing maleimide groups, i.e., (α) and (β), and, optionally, the hydroxylated organosilicon compounds (γ) is prepared and melted in the absence of a catalyst at a temperature at most equal to the melting point of the most difficult maleimide to liquefy, generally a temperature of from 50° to 300° C. If the reaction mixture comprises an organosilicon compound which is rich in hydroxyl groups, the mixture is maintained, in this case, in the molten state such as to achieve partial oligomerization of the silanediol; this compound will preferably be heated at approximately 150° C. until approximately 40% of the initial hydroxyl groups disappear during the oligomerization of this compound. In another embodiment, such oligomerization may be carried out before the introduction of the compounds containing maleimide groups.

The imidazole compound (δ) and, where appropriate, the N,N',N"-tris(hydroxyalkyl)hexahydrotriazine are then added to the mixture, which is well stirred, to permit them to be dispersed quickly.

When the catalyst is particularly active, in order to prevent it from becoming encapsulated in the polymer network it generates, it is desirable to add it together with a solvent which is compatible with the reaction medium. Thus, a solvent such as triallyl isocyanurate, diallyl phthalate or allyl benzoate may be employed.

A volatile solvent which will subsequently be removed by vaporization under reduced pressure may also be employed. In fact, the mixture is degassed in order to remove volatile products, the presence of which is detrimental for the preparation of laminates. The mixture is cast immediately after homogenization.

According to a second method, which can be carried out essentially in the absence of the hydroxylated organosilicon compound (γ), the compositions according to the invention may be produced by directly heating the compounds containing maleimide groups, i.e., (α) and (β), and the imidazole compound (δ) and, where appropriate, the N,N',N"-tris(hydroxyalkyl)hexahydrotriazine, optionally dissolved in a solvent, at a temperature ranging from 50° C. to 300° C., until a homogeneously liquid mixture is obtained. The mixture is then degassed and a resin is quickly cast after homogenization. Alternatively, this method may be carried out by first preparing an intimate admixture of mixture (β) and the imidazole compound (δ) and, where appropriate, the N,N',N"-tris(hydroxyalkyl)hexahydrotriazine, optionally dissolved in a solvent, and then adding compound (α) to the abovementioned mixture, which is heated to a temperature ranging from 50° C. to 300° C., until a homogeneous liquid mixture is obtained.

The thermosetting compositions according to the invention have a sufficient adhesiveness for applications such as laminates and composite materials.

The compositions may be employed for molding or impregnation operations. They may be used for the production of coatings, adhesive bondings, laminates and reinforced composite materials. The reinforcing material may be in the form of woven or non-woven fabrics, of unidirectional components or of natural or synthetic cut fibers such as glass, boron, carbon, tungsten, silicon or aromatic polyamide or polyamide-imide filaments or fibers. The compositions are of very particular advantage in the production of preimpregnated intermediate shaped articles without using solvent. The fibrous material may be impregnated by common techniques such as immersion, knife or curtain coating, or impregnation by transfer. The transferable film and preimpregnated shaped articles may be employed directly or stored for later use; they retain their properties very satisfactorily during cold storage at a temperature of from 0° to 10° C.

The impregnated materials may be used for the production of parts having different shapes and functions in many industries such as, for example, in aeronautics. These parts, which may be solids of rotation, are produced by placing or stacking several layers of preimpregnated materials on a form or support.

Crosslinking is then carried out under conventional conditions in this art relating to composite materials and especially at temperatures of from 100° to 300° C.

The preimpregnated materials may also be used as reinforcing pieces or as means for repairing worn-out parts.

However, it is also possible to design parts according to techniques of filament winding, with or without support, injection molding or pultrusion.

Shaped articles having high mechanical strength and thermoresistance may thus be produced.

In order to further illustrate the present invention and the advantages thereof, the following specific examples are given, it being understood that same are intended only as illustrative and in nowise limitative.

EXAMPLE 1

This example illustrates the preparation of a mixture according to this invention based on the following constituents: N-(3-allyloxyphenyl)maleimide + N-(3-allyloxy-4-allylphenyl)maleimide + N-(3-allyloxy-6-allylphenyl)maleimide + N-(3-allyloxy-4,6-diallylphenyl)maleimide.

1. First stage:

The following materials were charged into a glass reactor equipped with a central stirrer, a reflux condenser, a pH electrode, a temperature probe and a heating or cooling system:

186 g of maleic anhydride; and
540 cm³ of methyl isobutyl ketone; and heated to 40° C.

A solution of 196 g of meta-aminophenol in 1.2 liters of methyl isobutyl ketone was prepared and this solution was added to the reactor over the course of 1 hour; during this time period, the temperature increased from 40° C. to 60° C. When the addition was complete, the reaction was permitted to proceed, still at 60° C., for 20 minutes.

At the end of this stage, N-(3-hydroxyphenyl)-maleamic acid was produced. The yield was 100% relative to the starting aminophenol.

2. Second stage:

720 cm³ of water and 240 cm³ of aqueous 30% by weight sodium hydroxide were added to the reaction medium obtained at the end of the first stage and the pH of the medium was then adjusted to a value of 10.5 using the abovementioned aqueous sodium hydroxide. The temperature was then increased to 70° C. and 413 g of allyl chloride were added over the course of 4 hours. During this period, the temperature increased to 80° C. When the addition was complete, this temperature was maintained for an additional 2 hours. During the addition of the allyl chloride, the pH was maintained at a value of 10.5 by injecting aqueous 30% sodium hydroxide.

At the end of this stage, the pH was adjusted to a value in the region of 1 by adding an aqueous 50% by weight sulfuric acid solution and the aqueous phase was then removed by phase separation and an organic reaction mass ranging to 2150 g was obtained.

The yields, relative to the hydroxyphenylmaleamic acid, were as follows:

77% of N-(3-allyloxyphenyl)maleamic acid;
20% of N-(3-allyloxy-4-allylphenyl)maleamic and N-(3-allyloxy-6-allylphenyl)maleamic acids; and
3% of N-(3-allyloxy-4,6-diallylphenyl)maleamic acid.

3. Third stage:

3.2 cm³ of an aqueous 20% by weight solution of nickel acetate were added to the final medium from the second stage and 72.5 cm³ of water remaining in the organic phase were azeotropically distilled.

204 g of acetic anhydride and 51 g of triethylamine were then charged. The reaction mixture was heated at 65° C. for 1 hour, 30 minutes, and it was then cooled to 20° C. 800 cm³ of water were then added and the pH was adjusted to a value of 7 by adding aqueous 30% sodium hydroxide.

The aqueous phase was removed and the organic phase was washed with 2×100 cm³ of water. The solvent in the organic phase was distilled at a reduced pressure of 1.33×10² Pa, at approximately 50°-60° C. 250 g of a viscous oil, constituting the crude reaction product, were thus obtained.

The overall molar yields, relative to the starting aminophenol, were as follows:

40% of N-(3-allyloxyphenyl)maleimide:
10% of N-(3-allyloxy-4-allylphenyl)maleimide and N-(3-allyloxy-6-allylphenyl)maleimide; and
1.5% of N-(3-allyloxy-4,6-diallylphenyl)maleimide.

The crude reaction product was a mixture consisting of the following:

74.5% by weight of N-(3-allyloxyphenyl)maleimide;
21.8% by weight of N-(3-allyloxy-4-allylphenyl)-maleimide and N-(3-allyloxy-6-allylphenyl)maleimide; and
3.7% by weight of N-(3-allyloxy-4,6-diallylphenyl)-maleimide.

EXAMPLE 2

20 g of the crude product resulting from the process described in Example 1 were introduced into a glass reactor equipped with a side tube and an anchor type stirrer. The reactor was placed in an oil bath heated beforehand to 160° C. After homogenization for 2 minutes, a mixture of powders consisting of 68 g of N,N-4,4'-diphenylmethanebis-maleimide and 10 g of diphenylsilanediol was added, under stirring at 160° C., over the course of 4 minutes.

The reaction mass became clear in 7 minutes and the temperature was lowered to 150° C. and the reaction was permitted to proceed for an additional 7 minutes, and the mixture was then cooled to 130° C. over 15 minutes. A reduced pressure of approximately 130 Pa was then applied for 4 minutes.

Atmospheric pressure was then restored in the reactor and a catalytic solution of 0.1 g of imidazole in 1.9 g of triallyl isocyanurate was then introduced over the course of 1 minute. The mixture was then homogenized for 4 minutes and a reduced pressure of approximately 130 Pa was applied for 5 minutes.

The reaction mass was then cast into a mold which was preheated to 120° C. Sheets of size 140×100×4 mm were thus prepared, which were subjected to the following heat treatment cycle:

60 min between 120° C. and 150° C.;
60 min at 150° C.;
40 min between 150° C. and 200° C.;
120 min at 200° C.;
40 min between 200° C. and 250° C.;
16 hr at 250° C.;
and 2 hr between 250° C. and 25° C.

The heat-treated resin sheets thus obtained were opaque and defect-free. They were then cut to produce specimens of size 30×7×4 mm, and from which, breaking strength and Young's modulus under three point flexion (distance between supports 25.4 mm; INSTRON apparatus) were determined.

The values for the mechanical properties are reported in the following table:

Time 0:

| Temperature | $S_f$(MPa) | $M_f$(MPa) |
| --- | --- | --- |
| 25° C. | 123 | 2,700 |
| 250° C. | 64.7 | 2,200 |

-continued

After 1,000 hr at 250° C.:

| Temperature | $S_f$(MPa) | $M_f$(MPa) |
| --- | --- | --- |
| 25° C. | 102.3 | 3,000 |
| 250° C. | 54.4 | 2,420 |

EXAMPLE 3

19.35 g of the crude product resulting from the process described in Example 1 and 0.08 g of imidazole were introduced at ambient temperature into the reactor described in Example 2.

The reactor was placed in an oil bath which was preheated to 160° C. The mixture was stirred for 2 minutes to homogenize the catalyst. 60.64 g of N,N'-4,4'-diphenylmethanebis-maleimide were then added over the course of 5 minutes, under stirring. Two minutes after completion of the addition, the reaction mass was homogeneous. The reaction was permitted to proceed for an additional 5 minutes and a reduced pressure of 130 Pa was applied for 2 minutes.

The reaction mass was then cast into a mold which was preheated to 150° C. The prepolymer obtained was thus cast and then cured and tested as mentioned above in Example 2. It should be noted that the heat treatment cycle in this case was as follows:

1 hr at 150° C.;
50 min from 150° C. to 200° C.;
2 hr at 200° C.;
50 min from 1200° C. to 250° C.;
16 hr at 250° C.;
and 2 hr from 250° C. to 25° C.

Results of flexion of the cured polymer specimens:
at 25° C.: $S_f$=134 MPa: $M_f$=3,100 MPa:
at 250° C.: $S_f$=90.6 MPa: $M_f$=2,700 MPa

EXAMPLE 4

The reaction was carried out as in Example 3, using the following charges:

75.8 g of N,N'-4,4'-diphenylmethanebis-maleimide;
24.2 g of the crude product resulting from the process of Example 1; and
0.1 g of imidazole.

The reaction mass was poured onto cold plates 15 minutes after the completion of addition of the bis-maleimide.

The prepolymer was finely ground to give a yellow powder having a softening point of 77.6° C. This prepolymer was soluble to the extent of 50% (w/w) in cyclohexane and the collodion obtained was stable for at least 5 days; the properties of the resulting collodion were as follows:

gel time at 150° C.=42.6 min.
dynamic viscosity at 25° C.: time zero=1.64 poises, after 24 hr=2.1 poises Using this collodion, it was possible to produce 6-ply fiberglass (fabric 7628 marketed by Porcher having a weight of 200 g/m²; this fabric had undergone a treatment with gamma-aminopropyltriethoxysilane A 1100, marketed by Union Carbide) laminates (size 145×100 mm), by coating.

After drying for 5 minutes at 150° C., a 35 micrometer-thick copper strip was applied to each of the face surfaces of the laminate and the following heat treatment cycle was carried out:

15 min at 160° C.+1 hr, 15 min, at 180° C. under 40 bars, and 4 hr at 235° C.

The peel strength of the copper determined with an INSTRON apparatus, using a 90° angle of pull for the copper, was on the order of 14.7 N/cm.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. N-[(meth)allyloxy-(meth)allylphenyl]maleimide.
2. N-[(meth)allyloxy-di(meth)allylphenyl]maleimide.
3. N-[(meth)allyloxy(meth)allylphenyl]maleamic acid.
4. N-[(meth)allyloxy-di(meth)allylphenyl]maleamic acid.

* * * * *